United States Patent
Lu et al.

(10) Patent No.: US 10,710,915 B2
(45) Date of Patent: Jul. 14, 2020

(54) GRAPHENE AEROGEL METALLIC ORGANIC FRAME COMPOSITE MATERIAL LOADED WITH MICROORGANISM AS WELL AS PREPARATION METHOD AND APPLICATION THEREOF IN THE TREATMENT OF AZO DYE

(71) Applicant: SOOCHOW UNIVERSITY, Suzhou (CN)

(72) Inventors: Jianmei Lu, Suzhou (CN); Dongyun Chen, Suzhou (CN); Jun Jiang, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 0 days.

(21) Appl. No.: 16/427,071

(22) Filed: May 30, 2019

(65) Prior Publication Data
US 2019/0367395 A1   Dec. 5, 2019

(30) Foreign Application Priority Data
May 31, 2018 (CN) .......................... 2018 1 0547796

(51) Int. Cl.
C02F 3/34 (2006.01)
C02F 1/28 (2006.01)
C02F 1/20 (2006.01)
C12N 1/20 (2006.01)
C02F 101/30 (2006.01)
C02F 101/38 (2006.01)

(52) U.S. Cl.
CPC ............... *C02F 3/348* (2013.01); *C02F 1/28* (2013.01); *C12N 1/20* (2013.01); *C02F 1/283* (2013.01); *C02F 1/285* (2013.01); *C02F 2101/308* (2013.01); *C02F 2101/38* (2013.01)

(58) Field of Classification Search
CPC .. C02F 3/348; C02F 1/28; C02F 1/283; C02F 1/285; C02F 2101/308; C02F 2101/38; C02F 2003/001; C02F 3/341; C02F 1/288; C02F 3/34; C12N 1/20
USPC ........ 210/615, 616, 617, 150, 151; 435/177, 435/180, 182
See application file for complete search history.

(56) References Cited

U.S. PATENT DOCUMENTS

| | | | |
|---|---|---|---|
| 2015/0068974 A1* | 3/2015 | Kong | C09K 3/32 210/502.1 |
| 2015/0114907 A1* | 4/2015 | Gong | C08B 15/02 210/660 |
| 2017/0129786 A1* | 5/2017 | Chen | C02F 1/288 |

FOREIGN PATENT DOCUMENTS

WO   WO 2015/112088 A3 *  7/2015
WO   WO 2016/191802 A1 * 12/2016

* cited by examiner

*Primary Examiner* — Fred Prince
(74) *Attorney, Agent, or Firm* — SZDC Law P.C.

(57) ABSTRACT

The invention discloses a preparation method of a graphene aerogel metallic organic frame composite material loaded with microorganism as well as preparation method and application thereof in the treatment of azo dye. By using a hydrothermal method, a GA/MIL-100 graphene aerogel metallic organic frame composite material is successfully prepared, and in addition, the composite material disclosed by the invention has good adsorption and degradation effects on an azo dye. In addition, an adsorption method and a biological method are effectively combined, advantages of the two methods are taken into play, and a good application prospect can be achieved.

17 Claims, 4 Drawing Sheets

GRAPHENE AEROGEL METALLIC ORGANIC FRAME COMPOSITE MATERIAL LOADED WITH MICROORGANISM AS WELL AS PREPARATION METHOD AND APPLICATION THEREOF IN THE TREATMENT OF AZO DYE

This application claims priority to Chinese Patent Application No.: 201810547796.0, filed on May 31, 2018, which is incorporated by reference for all purposes as if fully set forth herein.

FIELD OF THE INVENTION

The present invention belongs to the technical field of composite material preparation, and particularly relates to a preparation method of graphene aerogel and metallic organic frame MIL-100 composite material loaded with microorganism and its application in the treatment of azo dyes.

TECHNICAL BACKGROUND

With the rapid development of economy, environmental issues are particularly prominent, causing people's strong concern. As a synthetic dye, azo dyes have a wide range of applications in industry, such as paper making, leather, cosmetics, food processing, etc. However, due to improper use and poor supervision, the living environment of people has been greatly affected. The removal of dyes from dye wastewater has therefore become an important issue in the field of water pollution, which has attracted worldwide attention. Initially, the adsorption method, as a simple and direct method with obvious adsorption effect, attracts people's attention, but the high cost, secondary pollution and low recycling utilization hinder its development. Therefore, finding an economic and sustainable method has become a hot topic at domestic and foreign research. The biological method has the advantages of economy, environmental protection and sustainability, so as to attract people's attention. But if the microorganism is used directly to degrade the dye, the degradation time is longer, and the high concentration of the dye also affects the microorganism. So, the simple use of microorganisms has been limited in practice.

SUMMARY OF THE INVENTION

The invention aims to introduce a graphene aerogel binding MOFS (metallic organic framework) composite material and a preparation method thereof, and uses the same in the treatment of azo dyes, the metallic organic framework is modified onto the graphene aerogel and combined with microorganisms to achieve local enrichment and separation of the dye, and the treatment effect on the azo dye is achieved.

In order to achieve the above object, the present invention provides a preparation method as follows:

A preparation method of graphene aerogel and metallic organic framework composite material loaded with microorganisms, including the following steps:

(1) mixing a graphene oxide solution with ascorbic acid and then placing it successively in a boiling water bath environment, an ice bath environment, a room temperature environment, a boiling water bath environment, and then performing freeze drying and thermal annealing to obtain a graphene aerogel;

(2) sequentially immersing the graphene aerogel in a silane coupling agent solution and a terephthalic acid solution to obtain a carboxylated graphene aerogel;

(3) using $FeCl_3$ ethanol solution and trimesic acid ethanol solution as self-assembly solution, the carboxylated graphene aerogel is self-assembled with layer-by-layer method to obtain graphene aerogel metallic organic framework composite material;

(4) loading microorganisms onto the surface of the graphene aerogel metallic organic framework composite material to obtain a graphene aerogel metallic organic framework composite material loaded with microorganisms.

The present invention also discloses a preparation method of a graphene aerogel metallic organic framework composite material, including the following steps:

(1) mixing a graphene oxide solution with ascorbic acid and then placing it successively in a boiling water bath environment, an ice bath environment, a room temperature environment, a boiling water bath environment, and then performing freeze drying and thermal annealing to obtain a graphene aerogel;

(2) sequentially immersing the graphene aerogel in a silane coupling agent solution and a terephthalic acid solution to obtain a carboxylated graphene aerogel;

(3) using $FeCl_3$ ethanol solution and trimesic acid ethanol solution as self-assembly solution, the carboxylated graphene aerogel is self-assembled with layer-by-layer method to obtain graphene aerogel metallic organic framework composite material.

The present invention also discloses a preparation method of a carboxylated graphene aerogel, including the following steps:

(1) mixing a graphene oxide solution with ascorbic acid and then placing it successively in a boiling water bath environment, an ice bath environment, a room temperature environment, a boiling water bath environment, and then performing freeze drying and thermal annealing to obtain a graphene aerogel;

(2) sequentially immersing the graphene aerogel in a silane coupling agent solution and a terephthalic acid solution to obtain a carboxylated graphene aerogel.

The present invention also discloses a method for treating azo dyes, including the following steps:

(1) mixing a graphene oxide solution with ascorbic acid and then placing it successively in a boiling water bath environment, an ice bath environment, a room temperature environment, a boiling water bath environment, and then performing freeze drying and thermal annealing to obtain a graphene aerogel;

(2) sequentially immersing the graphene aerogel in a silane coupling agent solution and a terephthalic acid solution to obtain a carboxylated graphene aerogel;

(3) using $FeCl_3$ ethanol solution and trimesic acid ethanol solution as self-assembly solution, the carboxylated graphene aerogel is self-assembled with layer-by-layer method to obtain graphene aerogel metallic organic framework composite material;

(4) loading microorganisms onto the surface of the graphene aerogel metallic organic framework composite material to obtain a graphene aerogel metallic organic framework composite material loaded with microorganisms;

(5) adding the graphene aerogel metallic organic framework composite material loaded with microorganisms into azo dye solution to complete the treatment of azo dye.

In the above technical solution, in step (1), the mass ratio of graphene oxide to ascorbic acid is 1:2; the time in boiling water bath environment, ice bath environment, room temperature environment, boiling water bath environment is respectively 30 minutes, 30 minutes, room temperature to thawing, 8 hours and thermal annealing at 200° C. in air for 2 h.

In the above technical solution, in step (2), the solvent in the silane coupling agent solution is ethanol, and the solvent in the terephthalic acid solution is DMF.

In the above technical solution, in step (3), the carboxylated graphene aerogel is sequentially immersed in $FeCl_3$ ethanol solution and trimesic acid ethanol solution as one self-assembly round, after repeated several rounds, the carboxylated graphene aerogel is obtained; the time of immersing in the $FeCl_3$ ethanol solution is 20 minutes, and the temperature of immersing in the trimesic acid solution is 70° C., time is 40 minutes.

In the above technical solution, in step (4), the graphene aerogel metallic organic framework composite is activated by NHS, DCC and DMAP; then the microorganism and the activated graphene aerogel metallic organic framework composite are dispersed in PBS, and shaken under a constant temperature shaker to obtain graphene aerogel metallic organic framework composite material loaded with microorganisms.

The present invention also discloses a graphene aerogel and metallic organic framework composite material loaded with microorganisms, a graphene aerogel metallic organic framework composite material, and a carboxylated graphene aerogel prepared by the above preparation method. Also with the application of a graphene aerogel and metallic organic framework composite material loaded with microorganisms, a graphene aerogel metallic organic framework composite material, or a carboxylated graphene aerogel in the treatment of azo dyes.

The preparation method of the graphene aerogel metallic organic framework composite loaded with *P. putida* of the invention could be carried out as follows:

(1) Preparation of GA

GO (graphene oxide) solution is mixed with ascorbic acid in a cylindrical glass vial, which is then placed in boiling water bath to obtain a partially reduced GO dispersion. The vial is then frozen in the freezer. After being thawed at room temperature, the vial is placed in a boiling water bath to further reduce GO. The obtained gel is then freezing drying and thermal annealing for 2 h to obtain graphene aerogel.

(2) Preparation of GA/MIL-100(Fe)

The graphene aerogel is sequentially immersed in a silane coupling agent and a terephthalic acid solution to obtain carboxylated graphene aerogel;

Carboxylated graphene aerogel is placed in $FeCl_3$ in ethanol for 20 min, then put into trimesic acid ($H_3BTC$) ethanol solution at 70° C. for 40 min. After each reaction, the product ished with ethanol. After repeated several times, the obtained products are ished with ultra-pure water and ethanol.

(3) The preparation of the graphene aerogel metallic organic framework composite loaded with *P. putida*

The microorganisms is loaded onto the surface of the graphene aerogel metal-organic framework composite to obtain GA/MIL-100 (Fe).

The present invention has the advantages as followed:

(1) The GA/MIL-100 graphene aerogel metallic organic framework composite prepared by the invention has simple preparation method, low cost of raw materials and is easy to obtain. The experimental test methods and experimental instruments involved are relatively common.

(2) The GA/MIL-100 prepared by the method of the invention can effectively realize the adsorption and biodegradation of azo dyes, and the raw material graphene has high stability and small pollution, with has good application prospects in energy and environmental protection.

(3) The graphene aerogel metallic organic frame composite material obtained by the invention has good adsorption effect and high degradation efficiency on azo dye, which can effectively combine adsorption method with biological method, and exerts the advantages of both.

DETAILED DESCRIPTION OF THE INVENTION

Implementation 1: Preparation of GO, the specific steps are as follows:

Graphite (3.0 g) and $NaNO_3$ (1.5 g) are mixed in concentrated $H_2SO_4$ (69 mL), and the mixture is cooled using an ice bath to 0° C. Then, KMnO4 (9.0 g) is added to the suspension slowly to keep the reaction temperature lower than 20° C. The reaction system is warmed to 35° C. and vigorously stirred for 7 h. Next, additional $KMnO_4$ (9.0 g) is added in one portion, and the reaction is still stirred at 35° C. for 12 h. After that, the reaction mixture is cooled to room temperature and poured into ice water (400 mL), then 30% $H_2O_2$ (3 mL) is added dropwise to reduce the residual $KMnO_4$ until no bubbles appeared, and the color of solution from brown turned to yellow. Then the mixture is centrifuged and washed with HCl (5%) to remove metal ions and rinsed with deionized water repeatedly to remove acid. The product is dispersed in deionized water to make a GO aqueous dispersion and then purified by dialysis for two weeks to remove the salt impurities and remaining acid. Subsequently, the solution is centrifuged at 11000 rpm for 20 min to remove redundant impurities. Finally, the supernatant liquor is obtained as GO solution and then is dried in vacuum desiccator to obtained GO.

Implementation 2: Preparation of GA, the specific steps are as follows:

GO solution (5 ml, 5 mg/mL) is mixed with ascorbic acid (50 mg) in a 20-ml cylindrical glass vial, which is then placed in boiling water bath for 30 min to obtain a partially reduced GO dispersion. The vial is then frozen in the freezer for 0.5 hours. After being thawed at room temperature, the vial is placed in a boiling water bath to further reduce GO for 8 h. The obtained gel is then sequentially subjected to dialysis in water (to remove soluble species), freezing drying and thermal annealing at 200° C. in air for 2 h.

Figure 1:
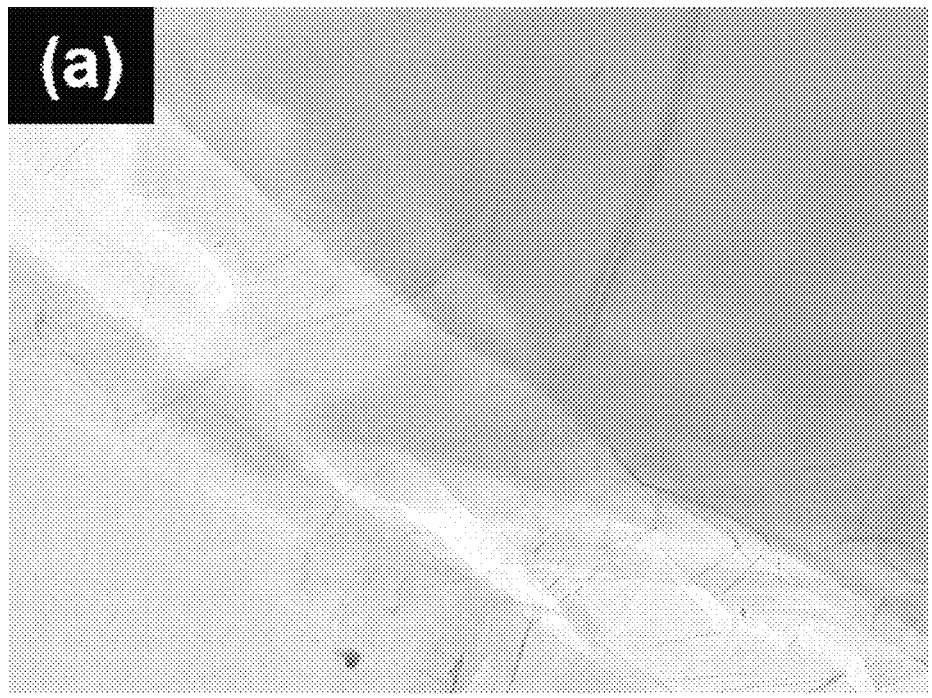
FIG. 1 shows the transmission electron microscope (TEM) of GO.
Figure 2:
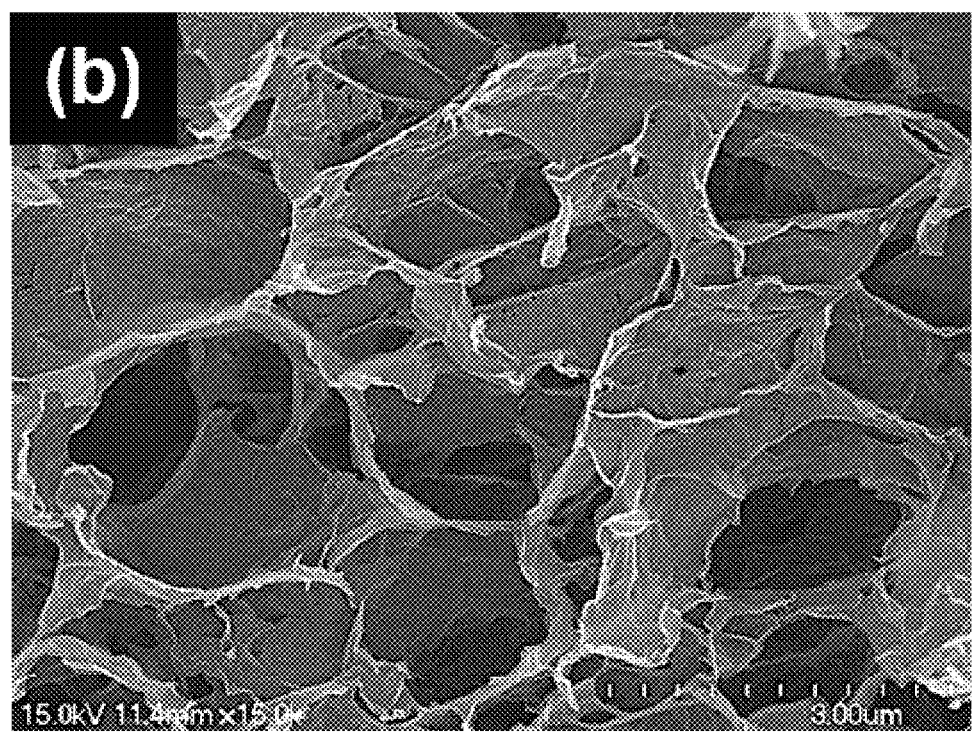
FIG. 2 shows the scanning electron micrograph (SEM) of GA.

FIG. 2 is a scanning electron micrograph of GA. It can be seen from the picture that the synthesized aerogel has a relatively uniform channel.

Implementation 3: Preparation of carboxylated graphene aerogel, the specific steps are as follows:

1 mL of (3-aminopropyl)triethoxysilane is dissolved in 40 mL of ethanol solution, and 100 mg GA is added gradually. After the mixture is oscillated for 8 h at room temperature, take it out and wash several times with ethanol, and then add to a DMF solution containing 0.45 grams of terephthalic acid. The mixture is then shaken for 8 hours, the obtained product is washed several times with ultra-pure water and ethanol to obtain carboxylated graphene aerogel.

Implementation 4: Preparation of GA/MIL-100(Fe), the specific steps are as follows:

100 mg of the product carboxylated GA obtained above is placed in 50 mL of $FeCl_3$ in ethanol (10 mM) for 20 min, then put into 50 mL of trimesic acid ($H_3BTC$) ethanol solution (10 mM) for 40 min at 70° C. After each reaction, the product washed with ethanol. After repeated several times, the obtained products are washed with ultra-pure water and ethanol to obtain graphene aerogel metal organic framework composite (GA/MIL-100 (Fe)).

Figure 3:
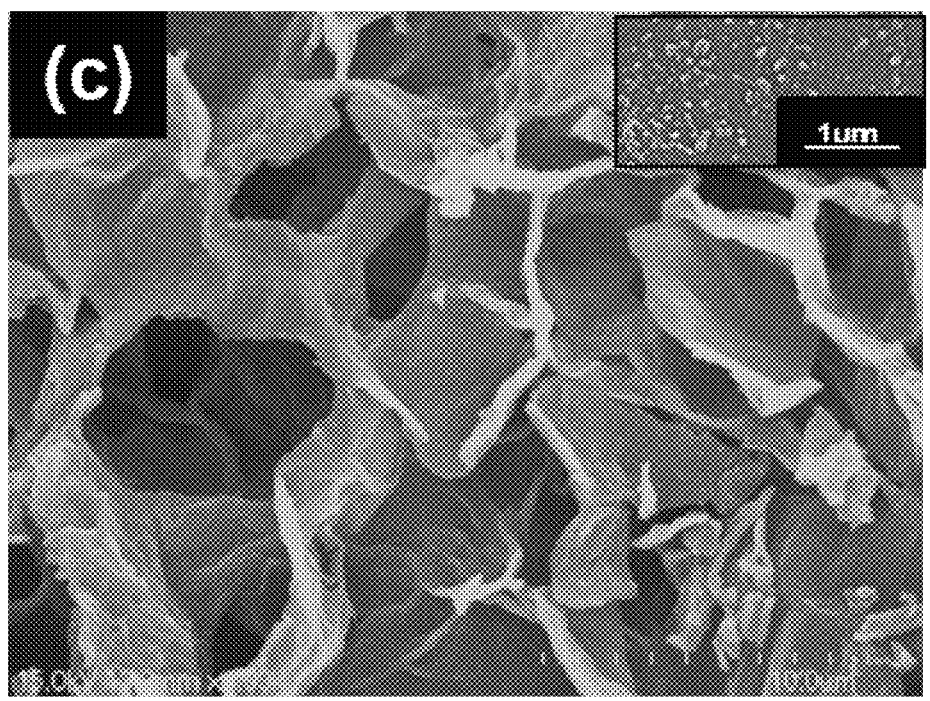
FIG. 3 shows the scanning electron micrograph (SEM) of GA/MIL-100.

FIG. 3 is a scanning electron micrograph of GA/MIL-100 (Fe). It can be seen from the picture that a large amount of MIL-100 (Fe) has been successfully incorporated into the aerogel, which proves that GA/MIL-100(Fe) has been successfully preparation.

Implementation 5: Preparation of GA/MIL-100 (Fe) loaded with *P. putida*, the specific steps are as follows:

Firstly, dried GA/MIL-100 (100 mg) and NHS (100 mg) are dispersed in DMF (40 mL) in a 100 mL beaker. DCC (300 mg) and DMAP (178 mg) are then added to the flask and oscillated for 24 h at room temperature, after that the product is washed with PBS for several times. Subsequently, After expanding the culture of *P. putida* in 50 mL LB liquid medium, the cells are centrifuged and washed with PBS for 3 times.

Then, 0.2 g wet weight of *P. putida* and activated GA/MIL-100 (Fe) are dispersed in 50 mL of PBS buffer and then reacted in the constant temperature oscillator at 30° C. and 150 r/min for about 24 h. Finally the final product is washed several times with the PBS buffer. The bacteria are firmly supported on the surface of the material by chemical bonding of the carboxyl functional group to the amino group on the surface of the bacteria.

Figure 4:
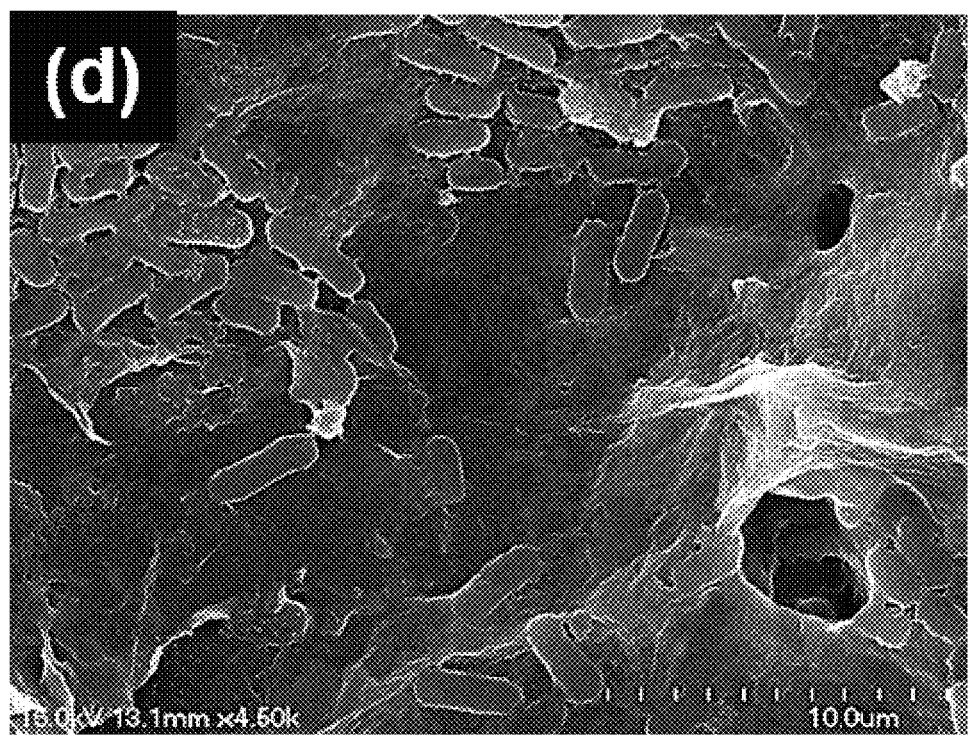
FIG. 4 shows scanning electron micrograph (SEM) of GA/MIL-100 loaded with *P. putida*.

FIG. 4 is a scanning electron micrograph of GA/MIL-100 (Fe) loaded with *P. putida*. It can be seen from the figure that *P. putida* has been firmly loaded onto GA/MIL-100 (Fe), which proves that the GA/MIL-100 graphene aerogel metal organic framework composite has been successfully prepared.

Implementation 6: The adsorption of azo dye by GA/MIL-100 (Fe), the specific steps are as follows:

In the adsorption experiment, 100 mg GA/MIL-100 (Fe) is added in 20 mL cylindrical glass vials containing 50 mg/L and 100 mg/L of AO10 solution, respectively, which sampled at different time intervals. The resulting sample is obtained by centrifugation and the residual concentration of AO10 is measured by a UV-visible spectrophotometer until the equilibrium concentration of the adsorption is no longer changed.

Figure 5:
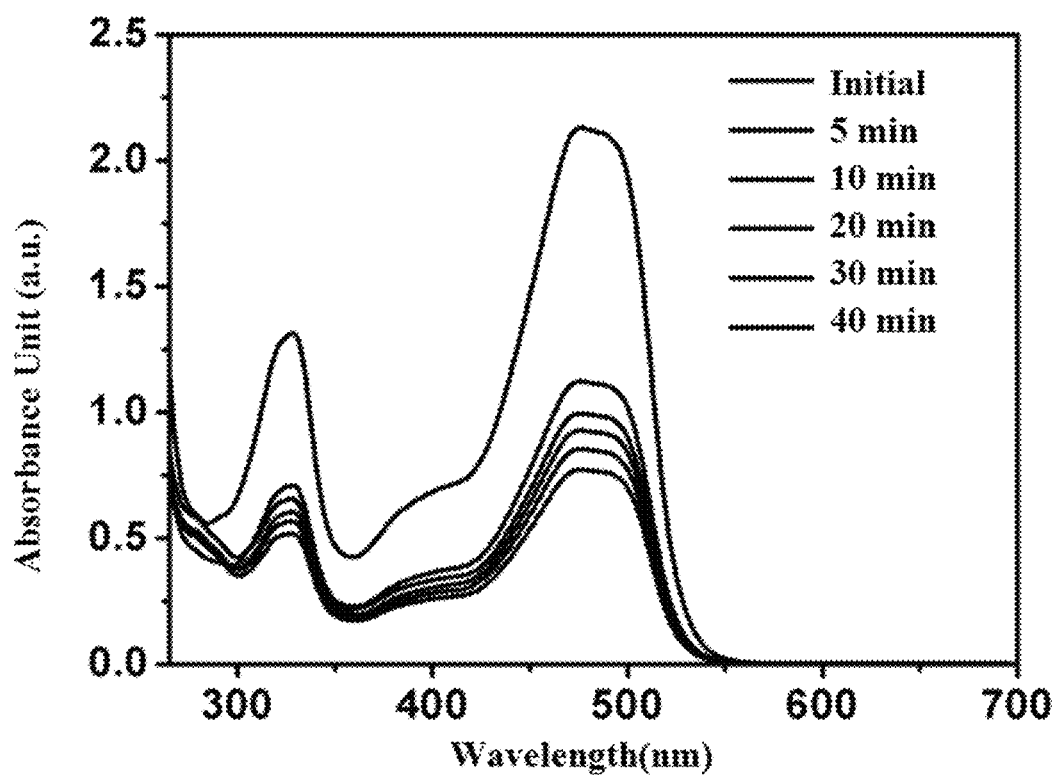
FIG. 5 shows the adsorption effect of GA/MIL-100 (Fe) on azo dyes (50 mg/L).
Figure 6:
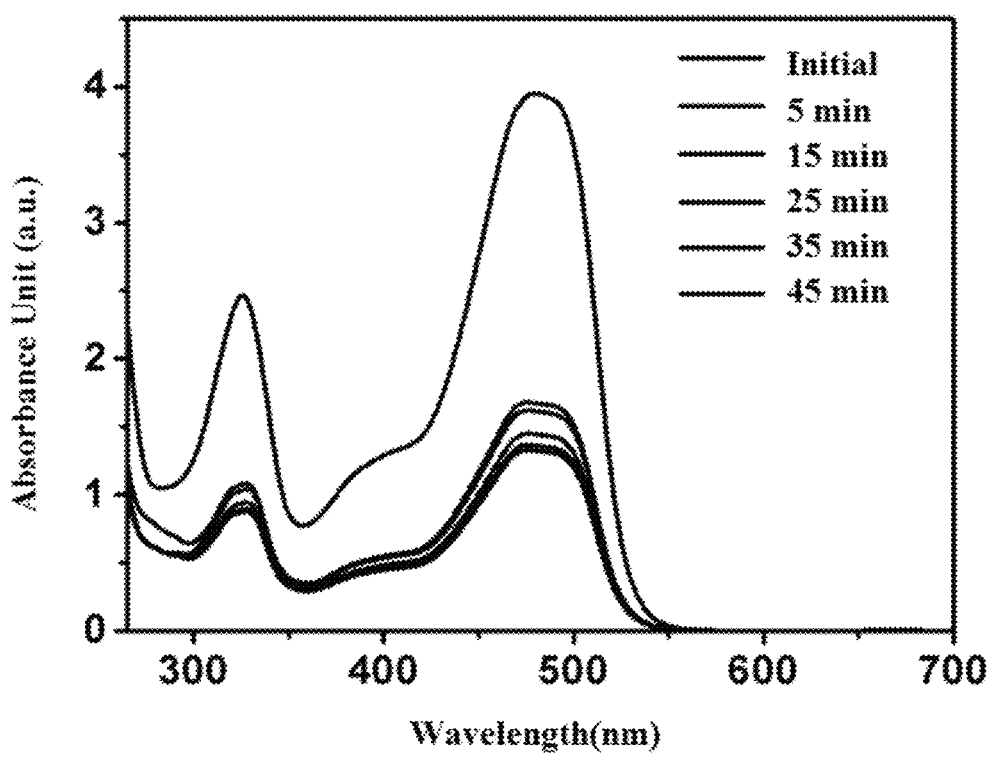
FIG. 6 shows the adsorption effect of GA/MIL-100 (Fe) on azo dyes (100 mg/L).

FIGS. 5 and 6 show the adsorption effect of GA/MIL-100 (Fe) on azo dyes (50, 100 mg/L). It can be seen from the picture that GA/MIL-100 (Fe) can be rapidly adsorbed in the initial stage, and then the speed is slowed down to reach the adsorption equilibrium, in which the balance time is 40 minutes and 45 minutes respectively.

Implementation 7: The degradation of azo dye by GA/MIL-100 (Fe) loaded with *P. putida*, the specific steps are as follows:

In the degradation experiment, 100 mg GA/MIL-100 (Fe) loaded with *P. putida*, is added in 20 mL cylindrical glass vials containing 50 mg/L and 100 mg/L of AO10 solution, respectively, which sampled at different time intervals. The resulting sample is obtained by centrifugation and the residual concentration of AO10 is measured by a UV-visible spectrophotometer until the equilibrium concentration of the adsorption is no longer changed.

Figure 7:
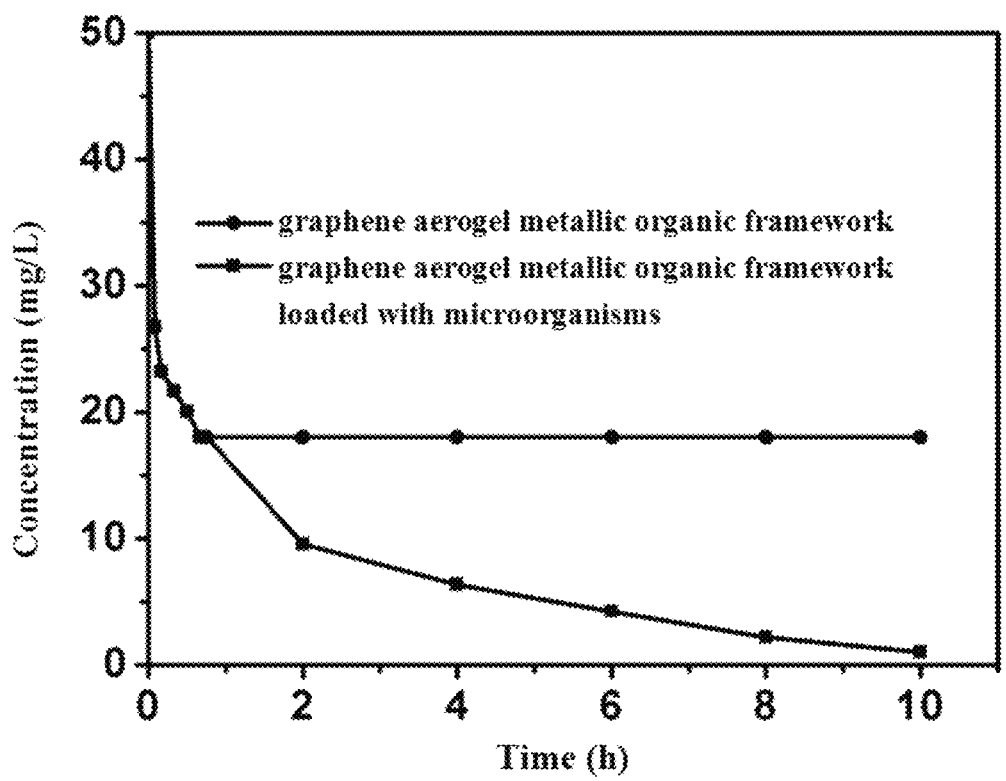
FIG. 7 shows the degradation effect of GA/MIL-100 (Fe) loaded with *P. putida* on azo dyes (50 mg/L).
Figure 8:
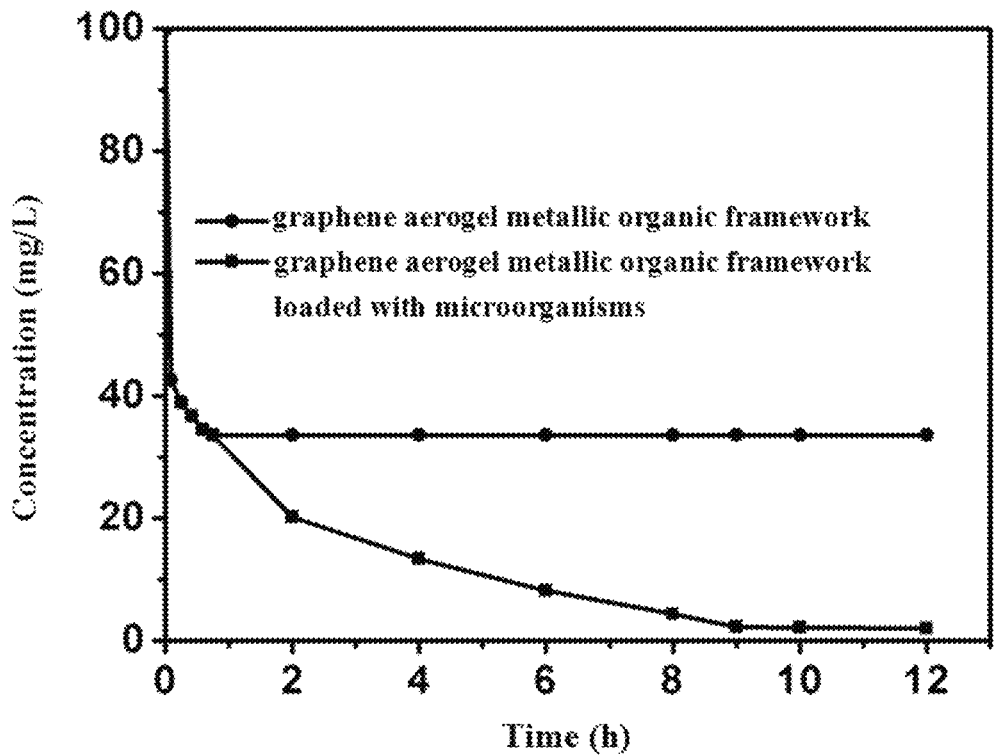
FIG. 8 shows the degradation effect of GA/MIL-100 (Fe) loaded with *P. putida* on azo dyes (100 mg/L).

FIGS. 7 and 8 are the degradation effects of GA/MIL-100 (Fe) loaded with *P. putida* on azo dyes (50, 100 mg/L). The whole process could be divided into the following two stages, the initial phase is the adsorption of GA/MIL-100 (Fe) azo dyes, followed by the degradation of the azo dye by GA/MIL-100 (Fe) loaded with *P. putida*.

Conclusion

Through the above analysis, the invention successfully prepared the GA/MIL-100 graphene aerogel metal organic framework composite by hydrothermal method, and the composite material disclosed by the invention has good adsorption and degradation effects on the azo dye. Moreover, the invention can effectively combine adsorption method with biological method and exerts the advantages of both, with a good application prospect.

We claim:

1. A preparation method of graphene aerogel and metallic organic framework composite material loaded with microorganisms, comprising the following steps:
   (1) mixing a graphene oxide solution with ascorbic acid and then placing it successively in a boiling water bath environment, an ice bath environment, a room temperature environment, a boiling water bath environment, and then performing freeze drying and thermal annealing to obtain a graphene aerogel;
   (2) sequentially immersing the graphene aerogel in a silane coupling agent solution and a terephthalic acid solution to obtain a carboxylated graphene aerogel;
   (3) using $FeCl_3$ ethanol solution and trimesic acid ethanol solution as self-assembly solution, the carboxylated graphene aerogel is self-assembled with layer-by-layer method to obtain graphene aerogel metallic organic framework composite material;
   (4) loading microorganisms onto the surface of the graphene aerogel metallic organic framework composite material to obtain a graphene aerogel metallic organic framework composite material loaded with microorganisms.

2. The method according to claim 1, further comprising:
   (5) adding the graphene aerogel metallic organic framework composite material loaded with microorganisms into azo dye solution to complete the treatment of azo dye.

3. A preparation method of a graphene aerogel metallic organic framework composite material, comprising the following steps:
   (1) mixing a graphene oxide solution with ascorbic acid and then placing it successively in a boiling water bath environment, an ice bath environment, a room temperature environment, a boiling water bath environment, and then performing freeze drying and thermal annealing to obtain a graphene aerogel;

(2) sequentially immersing the graphene aerogel in a silane coupling agent solution and a terephthalic acid solution to obtain a carboxylated graphene aerogel;

(3) using $FeCl_3$ ethanol solution and trimesic acid ethanol solution as self-assembly solution, the carboxylated graphene aerogel is self-assembled with layer-by-layer method to obtain graphene aerogel metallic organic framework composite material.

4. The method according to claim 3, wherein in step (1), the mass ratio of graphene oxide to ascorbic acid is 1:2; the time in boiling water bath environment, ice bath environment, room temperature environment, boiling water bath environment is respectively 30 minutes, 30 minutes, room temperature to thawing, 8 hours and thermal annealing at 200° C. in air for 2 h.

5. The method according to claim 3, wherein in step (2), the solvent in the silane coupling agent solution is ethanol, and the solvent in the terephthalic acid solution is DMF.

6. The method according to claim 3, wherein in step (3), the carboxylated graphene aerogel is sequentially immersed in $FeCl_3$ ethanol solution and trimesic acid ethanol solution as one self-assembly round, after repeated several rounds, the carboxylated graphene aerogel is obtained; the time of immersing in the $FeCl_3$ ethanol solution is 20 minutes, and the temperature of immersing in the trimesic acid solution is 70° C., time is 40 minutes.

7. The method according to claim 3, wherein in step (4), the graphene aerogel metallic organic framework composite is activated by NHS, DCC and DMAP; then the microorganism and the activated graphene aerogel metallic organic framework composite are dispersed in PBS, and shaken under a constant temperature shaker to obtain graphene aerogel metallic organic framework composite material loaded with microorganisms.

8. A preparation method of a carboxylated graphene aerogel, comprising the following steps:
    (1) mixing a graphene oxide solution with ascorbic acid and then placing it successively in a boiling water bath environment, an ice bath environment, a room temperature environment, a boiling water bath environment, and then performing freeze drying and thermal annealing to obtain a graphene aerogel;
    (2) sequentially immersing the graphene aerogel in a silane coupling agent solution and a terephthalic acid solution to obtain a carboxylated graphene aerogel.

9. The method according to claim 1, wherein in step (1), the mass ratio of graphene oxide to ascorbic acid is 1:2; the time in boiling water bath environment, ice bath environment, room temperature environment, boiling water bath environment is respectively 30 minutes, 30 minutes, room temperature to thawing, 8 hours and thermal annealing at 200° C. in air for 2 h.

10. The method according to claim 1, wherein in step (2), the solvent in the silane coupling agent solution is ethanol, and the solvent in the terephthalic acid solution is DMF.

11. The method according to claim 1, wherein in step (3), the carboxylated graphene aerogel is sequentially immersed in $FeCl_3$ ethanol solution and trimesic acid ethanol solution as one self-assembly round, after repeated several rounds, the carboxylated graphene aerogel is obtained; the time of immersing in the $FeCl_3$ ethanol solution is 20 minutes, and the temperature of immersing in the trimesic acid solution is 70° C., time is 40 minutes.

12. The method according to claim 1, wherein in step (4), the graphene aerogel metallic organic framework composite is activated by NHS, DCC and DMAP; then the microorganism and the activated graphene aerogel metallic organic framework composite are dispersed in PBS, and shaken under a constant temperature shaker to obtain graphene aerogel metallic organic framework composite material loaded with microorganisms.

13. A graphene aerogel and metallic organic framework composite material loaded with microorganisms prepared by the preparation method according to claim 1.

14. An application of a graphene aerogel and metallic organic framework composite material loaded with microorganisms, a graphene aerogel metallic organic framework composite material, or a carboxylated graphene aerogel according to claim 13 in treatment of azo dyes.

15. The method according to claim 8, wherein in step (1), the mass ratio of graphene oxide to ascorbic acid is 1:2; the time in boiling water bath environment, ice bath environment, room temperature environment, boiling water bath environment is respectively 30 minutes, 30 minutes, room temperature to thawing, 8 hours and thermal annealing at 200° C. in air for 2 h.

16. The method according to claim 8, wherein in step (2), the solvent in the silane coupling agent solution is ethanol, and the solvent in the terephthalic acid solution is DMF.

17. The method according to claim 8, wherein in step (4), the graphene aerogel metallic organic framework composite is activated by NHS, DCC and DMAP; then the microorganism and the activated graphene aerogel metallic organic framework composite are dispersed in PBS, and shaken under a constant temperature shaker to obtain graphene aerogel metallic organic framework composite material loaded with microorganisms.

\* \* \* \* \*